United States Patent

Unger et al.

[11] Patent Number: 4,968,717
[45] Date of Patent: Nov. 6, 1990

[54] PHENYLACETONITRILES WHICH ARE SUBSTITUTED BY BASIC GROUPS, THEIR PREPARATION AND DRUGS CONTAINING THESE SUBSTANCES

[75] Inventors: Liliane Unger, Ludwigshafen; Manfred Raschack, Weisenheim; Verena Baldinger, Heidelberg; Ferdinand Dengel, Wilhelmsfeld; Oskar Ehrmann, Mannheim; Hans J. Treiber, Bruehl; Werner Seitz, Plankstadt, all of Fed. Rep. of Germany

[73] Assignee: BASF Aktiengesellschaft, Ludwigshafen, Fed. Rep. of Germany

[21] Appl. No.: 351,036

[22] Filed: May 12, 1989

Related U.S. Application Data

[63] Continuation of Ser. No. 9,722, Feb. 2, 1987, abandoned.

[30] Foreign Application Priority Data

Jan. 31, 1986 [DE] Fed. Rep. of Germany ....... 3603032

[51] Int. Cl.⁵ .................. A61K 31/275; C07C 255/03; C07D 317/48
[52] U.S. Cl. ..................... 514/523; 514/456; 514/465; 514/466; 558/390; 549/437; 549/439; 549/440; 549/443; 549/435; 549/466; 549/365
[58] Field of Search ................ 558/390; 514/523, 456, 514/466, 465; 549/435, 366, 365, 437, 439, 440, 443

[56] References Cited

FOREIGN PATENT DOCUMENTS

| 1207797 | 7/1986 | Canada ............................ 558/390 |
| 47888 | 3/1982 | European Pat. Off. ............ 558/390 |
| 2059985 | 6/1972 | Fed. Rep. of Germany ...... 558/390 |
| 92732 | 8/1978 | Japan ................................ 558/390 |
| 1377209 | 12/1974 | United Kingdom ............... 558/390 |

OTHER PUBLICATIONS

Merck Index, 10th Ed.; 9747 (1981).
R. Mannhold et al., 31 Arzneim-Forsch/Drug Res., Nr. 5, pp. 773–780 (1981).

*Primary Examiner*—John M. Ford
*Assistant Examiner*—J. Richter
*Attorney, Agent, or Firm*—Keil & Weinkauf

[57] ABSTRACT

Compounds of the formula

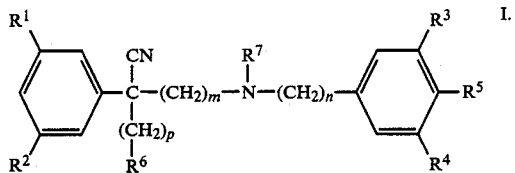

where $R^1$ to $R^7$, m, n and p have the meanings stated in the description, and certain derivatives which are p-substituted in the left-hand phenyl ring, are useful for the treatment of disorders.

5 Claims, No Drawings

PHENYLACETONITRILES WHICH ARE SUBSTITUTED BY BASIC GROUPS, THEIR PREPARATION AND DRUGS CONTAINING THESE SUBSTANCES

This application is a continuation of application Ser. No. 009,722, filed on Feb. 2, 1987, now abandoned.

The present invention relates to novel phenylacetonitriles which are substituted by basic groups, their preparation and drugs which contain these substances.

German Patent Nos. 1,154,810 and 1,493,904, German Laid-Open Applications DOS Nos. 1,593,921 and DOS 1,643,429 and European Laid-Open Applications Nos. 147,707 and 64,158 disclose phenylacetonitriles which are substituted by basic groups. Because they act as calcium antagonists, verapamil and gallopamil have proven useful in the therapy of coronary heart diseases and of high blood pressure. It is also known that the two active compounds have an antiserotonin action, which however is not very pronounced compared with known serotonin antagonists [J. E. Taylor and F. V. DeFeudis, Eur. J. Pharmacol. 106 (1984), 215–216 and M. Auguet, F. V. DeFeudis and F. Clostre, Neurochem. Int. 6 (5) (1984), 701–710].

It is known that serotonin is involved in producing spasms of central and peripheral vessels and in blood platelet aggregation, which leads to blockage of vessels, and, depending on the clinical symptoms, may even be more important in this respect than the excitation produced by calcium ions. Hence, both calcium antagonists and serotonin antagonists are used for such disorders. It is therefore particularly useful to have both active principles combined in one molecular structure.

We have found novel compounds whose antiserotonin action is so pronounced that they achieve the power of known serotonin antagonists but are several times more powerful than the comparative compounds verapamil and gallopamil. The calcium-antagonistic action of the novel compounds is fully retained.

The present invention relates to novel phenylacetonitriles which are substituted by basic groups and are of the formula I

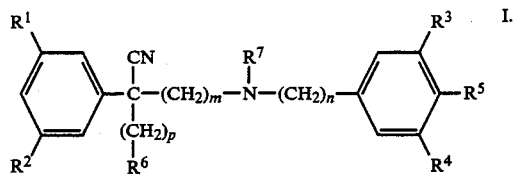

where
R¹ and R² are identical or different and are each hydrogen, halogen, $C_1$–$C_3$-alkyl, nitro, methoxy, ethoxy, trifluoromethoxy or $\beta,\beta,\beta$-trifluoroethoxy,
R³ and R⁴ are identical or different and are each hydrogen, halogen, trifluoromethyl, $C_1$–$C_3$-alkyl, nitro, methoxy or ethoxy,
R⁵ is hydrogen, halogen or $C_1$–$C_3$-alkyl, or
R³ and R⁵ together may furthermore form a methylenedioxy, ethylenedioxy, 1,3-dioxatetramethylene, propylene or butylene group, and one or more of the radicals R¹ to R⁵ must not be hydrogen and, if R⁶ is isopropyl, R⁷ is methyl, m is 3, n is 2 and p is 0, R¹, R², R³ and R⁴ cannot simultaneously be methoxy or ethoxy,
R⁶ is a saturated or unsaturated hydrocarbon radical of not more than 6 carbon atoms, $C_3$–$C_8$-cycloalkyl or $C_5$–$C_8$cycloalkenyl or is phenyl which is provided with R³, R⁴ or R⁵,
R⁷ is $C_1$–$C_4$-alkyl,
m is from 2 to 4,
n is 2 or 3 and
p is 0 or 1,
and their antipodes and salts with physiologically tolerated acids.

The present invention furthermore relates to the following phenylacetonitriles which are substituted by basic groups and their antipodes and salts with physiologically tolerated acids:
(RS)-5-[(3-methoxyphenethyl)-methylamino]-2-(3,4,5-trimethoxyphenyl)-2-isopropylvaleronitrile,
(RS)-5-[(3-nitrophenethyl)-methylamino]-2-(3,4,5-trimethoxyphenyl)-2-isopropylvaleronitrile,
(RS)-5-[(3-chlorophenethyl)-methylamino]-2-(3,4,5-trimethoxyphenyl)-2-isopropylvaleronitrile,
(RS)-5-[(1,3-benzodioxan-6-ylethyl)-methylamino]-2-(3,4,5-trimethoxyphenyl)-2-isopropylvaleronitrile,
(RS)-5-[(3-methoxyphenethyl)ethylamino]-2-(3,4,5-trimethoxyphenyl) 2-isopropylvaleronitrile,
(RS)-5-[(3,4-dichlorophenethyl)-methylamino]-2-(3,4-dimethoxyphenyl)-2-isopropylvaleronitrile,
(RS)-5-[(3,5-dimethoxyphenethyl)-methylamino]-2-(3,4-dichlorophenyl)-2-isopropylvaleronitrile,
(RS)-5-[(3,5-dimethoxyphenethyl)-methylamino]-2-(4-chlorophenyl)-2-isopropylvaleronitrile,
(RS)-5-[(3,5-dimethoxyphenethyl)-methylamino]-2-(1,2,3,4-tetrahydronaphth-2-yl)-2-isopropylvaleronitrile,
(RS)-5-[(3,4-dimethoxyphenethyl)-methylamino]-2-(3-ethoxy-phenyl)-2-isopropylvaleronitrile,
(RS)-5-[(3,4,5-trimethoxyphenethyl)-methylamino]-2-(3,5-dimethoxyphenyl)-2-isopropylvaleronitrile,
(RS)-5-[(3,4-dimethoxyphenethyl)-methylamino]-2-(3-ethoxy-phenyl)-2-isopropylvaleronitrile,
(RS)-5-[(3,4,5-trimethoxyphenethyl)-methylamino]-2-(3,5-dimethoxyphenyl)-2-isopropylvaleronitrile,
(RS)-5-[(3-fluoro-4-methoxyphenethyl)-methylamino]-2-(3,5-dimethoxyphenyl)-2-isopropylvaleronitrile,
(RS)-5-[(4-methoxyphenethyl)-methylamino]-2-(3,5-dimethoxyphenyl)-2-isopropylvaleronitrile,
(RS)-5-[(3,4-dimethoxyphenethyl)-methylamino]-2-(3,5-dimethoxyphenyl)-2-isopropylvaleronitrile and
(RS)-5-[(4-fluorophenethyl)-methylamino]-2-phenyl-2-isopropylvaleronitrile.

Finally, the present invention relates to the use of the compounds of the formula

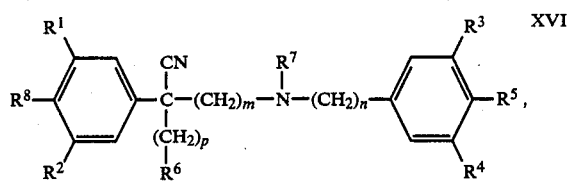

where
R¹, R², R³, R⁴, R⁵ and R⁸ are identical or different and are each hydrogen, halogen, trifluoromethyl, $C_1$–$C_3$-alkyl, nitro, methoxy, ethoxy, trifluoromethoxy or $\beta,\beta,\beta$-trifluoroethoxy, or R³ and R⁵ together may furthermore form a methylenedioxy, ethylenedioxy, 1,3-dioxatetramethylene, propylene or butylene group, $R^6$ is a saturated or unsaturated hydrocarbon radical of not more than 6 carbon atoms, $C_3$-$C_8$-cycloalkyl or $C_5$-$C_8$-cycloalkenyl or is a phenyl radical which is provided with $R^1$, $R^2$ or $R^3$, $R^7$ is $C_1$-$C_4$-alkyl, m is 2, 3 or 4, n is 2 or 3 and p is 0 or 1, and their antipodes and salts with physiologically tolerated acids for the preparation of drugs for the treatment of cerebrovascular disorders, hypertension, coronary heart disease, platelet aggregation and peripheral vascular disorders.

Examples of suitable physiologically tolerated acids are hydrochloric acid, sulfuric acid, phosphoric acid, acetic acid, malonic acid, succinic acid, fumaric acid, maleic acid, citric acid, tartaric acid, lactic acid and amidosulfonic acid.

Preferred halogen atoms $R^1$-$R^6$ are fluorine and chlorine. Preferred nitro compounds are those containing one nitro group.

The following compounds and their enantiomers are particularly important:

(RS)-5-[(3,5-dimethoxyphenethyl)-methylamino]-2-(3-methoxy-phenyl)-2-isopropylvaleronitrile, (RS)-5-[(3-methoxyphenethyl)-methylamino]-2-(3,5-dimethoxyphenyl)-2-isopropylvaleronitrile, (RS)-5-[(3-methoxyphenethyl)-methylamino]-2-(3-methoxy-phenyl)-2-isopropylvaleronitrile, (RS)-5-[(3,4-xylylethyl)-methylamino]-2-(3,5-dimethoxyphenyl)-2-isopropylvaleronitrile (RS)-5-[(3-methoxyphenethyl)-methylamino]-2-(3,4,5-trimethoxyphenyl)-2-isopropylvaleronitrile, (RS)-5-[(3-nitrophenethyl)-methylamino]-2-(3,4,5-trimethoxyphenyl)-2-isopropylvaleronitrile, (RS)-5-[(1,3-benzodioxan-6-ylethyl)-methylamino]-2-(3,4,5-trimethoxyphenyl)-2-isopropylvaleronitrile, (RS)-5-[(3,4-dichlorophenethyl)-methylamino]-2-(3,4-dimethoxyphenyl)-2-isopropylvaleronitrile, (RS)-5-[(3,5-dimethoxyphenethyl)-methylamino]-2-(3,4-dichlorophenyl)-2-isopropylvaleronitrile, (RS)-5-[(phenethyl)-methylamino]-2-(3,5-dimethoxyphenyl)-2-isopropylvaleronitrile.

The novel compounds are prepared by (a) reacting a phenylacetonitrile of the formula II

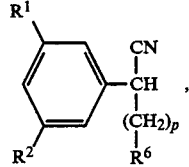

where $R^1$, $R^2$, $R^6$ and p have the stated meanings, with a 1-phenylazaalkane of the formula III

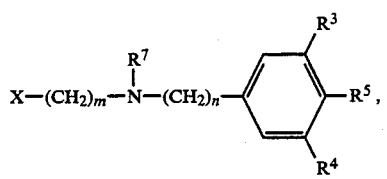

where $R^3$, $R^4$, $R^5$, $R^7$, m and n have the stated meanings and X is a leaving group, or (b) reacting a phenylacetonitrile which is substituted by basic groups and of the formula IV

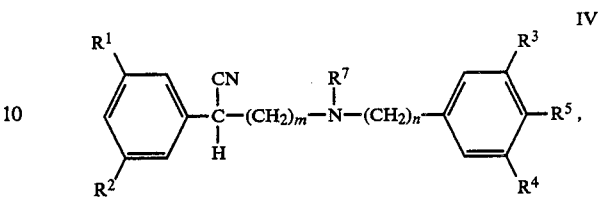

where $R^1$, $R^2$, $R^3$, $R^4$, $R^5$, $R^7$, m and n have the stated meanings, with a compound of the formula V

where $R^6$ and p have the stated meanings and Y is a leaving group, or (c) reacting a phenylacetonitrile of the formula VI

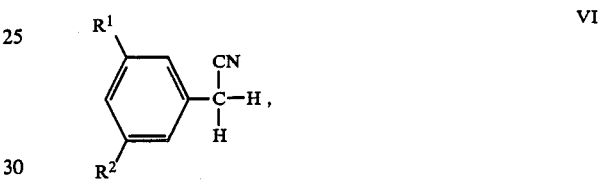

where $R^1$ and $R^2$ have the stated meanings, with a 1-phenylazaalkane of the formula III and a compound of the formula V, or (d) reacting a phenylacetonitrile of the formula VII

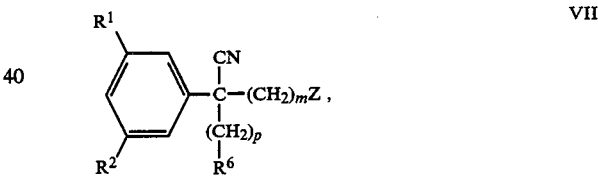

where $R^1$, $R^2$, $R^6$, m and p have the stated meanings and Z is a leaving group, with a phenylalkylamine of the formula VIII

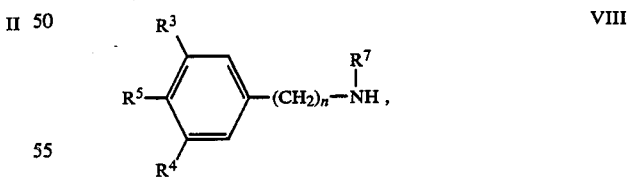

where $R^3$, $R^4$, $R^5$, $R^7$ and n have the above meanings, (e) reacting a phenylacetonitrile of the formula IX

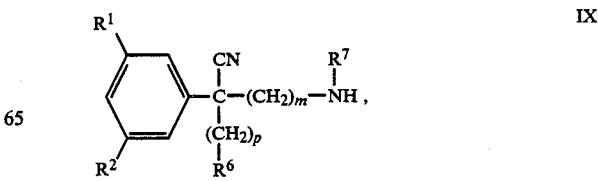

where $R^1$, $R^2$, $R^6$, $R^7$, m and p have the stated meanings, with a phenylalkyl derivative of the formula X

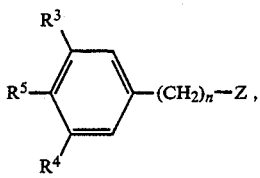

where $R^3$, $R^4$, $R^5$, n and Z have the above meanings, or (f) alkylating a phenylacetonitrile which is substituted by basic groups and of the formula XI

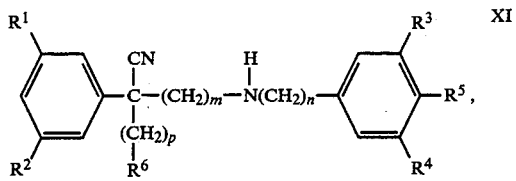

where $R^1$, $R^2$, $R^3$, $R^4$, $R^5$, $R^6$, m, n and p have the stated meanings, or (g) reacting a phenylacetonitrile of the formula IX with an aldehyde of the formula XII

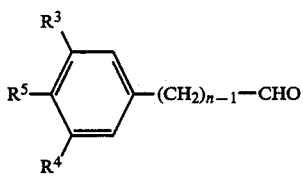

where $R^3$, $R^4$, $R^5$ and n have the above meanings, under reductive conditions, or (h) reacting an aldehyde of the formula XIII

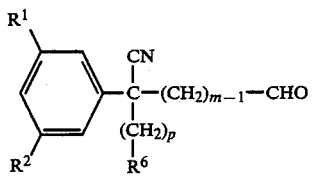

where $R^1$, $R^2$, $R^6$, m and p have the above meanings, with a phenylalkylamine of the formula VIII under reductive conditions, or (i) reducing a dinitrile of the formula XIV

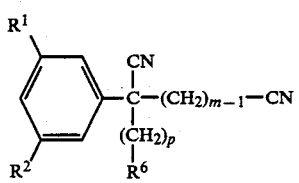

where $R^1$, $R^2$, m and p have the above meanings, in the presence of a phenylalkylamine of the formula VIII, or (k) reducing a nitrile of the formula XV

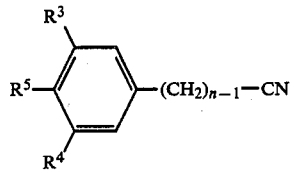

where $R^3$, $R^4$, $R^5$ and n have the above meanings, in the presence of a phenylacetonitrile of the formula IX, and if desired, resolving the resulting compound into its antipodes and/or converting it to a salt with a physiologically tolerated acid.

The other phenylacetonitriles which are not of the formula I can be prepared in a similar manner.

Reaction (a) can be carried out, for example, by metallizing a CH-acidic phenylacetonitrile of the formula II with a base in an inert solvent and then reacting the product with a compound of the formula III. If desired, it is also possible to adopt a procedure in which the base is added to a solution of compounds of the formulae II and III.

Suitable bases are alkali metal hydrides, hydroxides, alcoholates and amides and organometallic compounds. Sodium amide powder and suspension, potassium hydroxide powder, butyllithium and lithium diisopropylamide are preferably used.

Suitable solvents for the reaction are aromatic and aliphatic hydrocarbons, although fairly high boiling aliphatic ethers and dipolar aprotic solvents are also useful. Toluene is preferably employed.

Reaction (a) can also be carried out by phase transfer catalysis. Quaternary ammonium and phosphonium salts, crown ethers, polyethylene glycol dialkyl ethers (e.g. PEG 600 dibutyl ether) and tris-(3,6-dioxaheptyl)amine (TDA-1) are used as catalysts.

The reaction temperatures depend on the base used and are, for example, from 0° to $-100°$ C. when butyllithium is employed and preferably from 50° to 150° C. when sodium amide is used.

The reaction of compounds of the formula IV to form the novel compounds (process b) is carried out in a similar manner to (process a).

Examples of suitable reactants of the formula IV are alkane derivatives having a leaving group, such as halides, sulfuric esters, tosylates, mesylates or triflates.

In process c), the sequence of the addition of compounds III, V and VI can be chosen freely, and intermediates need not be isolated.

Reaction d) is carried out by simply heating the reactants, preferably at from 120° to 180° C. It can also be carried out in a solvent, although the latter is not required. The same applies to reaction e). In both cases, suitable radicals Z are halogen, preferably chlorine or bromine.

The alkylation f) is carried out using a dialkyl sulfate or alkyl halide in the presence of an acid acceptor, such as triethylamine or potassium carbonate. Advantageously, a solvent such as toluene or dipolar aprotic solvent such as dimethylformamide is used. The methylation may also be carried out by the Leuckart-Wallach method, using formaldehyde/formic acid.

In processes g) and h), the two reactants of the formulae IX and XII or XIII and VIII are subjected to a condensation reaction under reductive conditions.

Suitable solvents are aliphatic and aromatic hydrocarbons, halohydrocarbons, ethers, alcohols and lower fatty acids. The reaction temperatures are from 0° to 150° C., preferably from 20° to 70° C.

Suitable reducing agents are hydrogen in the presence of a catalyst, e.g. $PtO_2$, Pd/C or a nickel or cobalt catalyst, nascent hydrogen obtained from a metal and an acid, complex metal hydrides (e.g. $NaBH_4$) and hydride donors (e.g. formic acid).

The reduction of the dinitrile of the formula XIV in the presence of a phenylalkylamine of the formula VIII (reaction i) or of a nitrile of the formula XV in the presence of a phenylacetonitrile of the formula IX (reaction k) is preferably carried out as a catalytic hydrogenation using a noble metal catalyst, preferably Pd/C. The reaction temperatures are from 30° to 80° C., preferably 60° C. The reaction can be carried out under atmospheric or superatmospheric pressure of up to 6 bar. Lower alcohols, acetic acid or aromatic hydrocarbons, preferably lower aliphatic alcohols, such as ethanol, are used as solvents. From 0.1° to 10% by weight, based on the amine used, of Pd/C catalyst are required, the catalyst containing from 1 to 10% by weight of Pd on carbon.

If the reduction is carried out in the presence of a catalyst, atmospheric pressure is preferably employed.

Reactions (a) to (i) are described in German Pat. Nos. 1,154,810, 1,158,083, 2,059,923 and 2,631,222, German Published Application DAS Nos. 2,263,527, German Laid-Open Application DOS No. 3,034,221 and European Laid-Open Application No. 165,322.

The novel compounds possess one or more asymmetric carbon atoms. Consequently, they can be prepared either in the form of pure enantiomers or as racemic mixtures (cf. German Pat. Nos. 2,059,923 and 2,059,985. The racemates of the compounds I can be resolved into their optical antipodes by conventional techniques, for example by separation (fractional crystallization, column chromatography) of the diastereomeric salts. The latter can be prepared by reacting the compounds I with chiral acids. The enantiomers can also be obtained by using optically active starting compounds.

The starting materials of the formulae IV, VII, IX, X, XI, XIII and XIV which have not been described to date can be prepared as follows:

The compounds IV are obtained by reacting a phenylacetonitrile (VI) with a 1-phenyl-omega-haloazaalkane (cf. III) in the presence of sodium amide in toluene.

The compounds VII can be prepared by reacting a 1-cyano-1-phenylalkane (II) with chloropropanol and then reacting the resulting alcohol with, for example, thionyl chloride.

The compounds IX can be obtained from the phenylacetonitrile derivatives VII by reaction with alkylamines.

The substances of the formula X are prepared by hydrolyzing, for example, the phenylacetonitriles VI to give phenylacetic acid, reducing the latter to the corresponding alcohol and chlorinating this with, for example, thionyl chloride.

The reaction of a 1-cyano-1-phenylalkane (II) with a 1-phenyl-omega-haloazaalkane (cf: III) in the presence of sodium amide in toluene leads to the compounds XI.

The compounds XIII are obtained by reacting a 1-cyano-1-phenylalkane (II) with an omega-haloaldehyde diethyl acetal in the presence of sodium amide in toluene and then treating the resulting reaction product with an acid.

Dinitriles of the formula XIV are obtainable by an addition reaction of acrylonitrile with a phenylacetonitrile of the formula II.

The compounds possess useful pharmacological properties and are therefore suitable for the treatment of cardiovascular disorders, in particular cerebrovascular disorders, for example migraines, vasospasms, subarachnoid hemorrhage, apoplectic shock or cerebral ischemia, and for peripheral vascular disorders, such as Raynaud's disease, and coronary heart disease, hypertension and vasogenic shock.

Specific examples of compounds substituted in the left-hand phenyl ring by $R^8$ are:
(RS)-5-[(3-methoxyphenethyl)-methylamino]-2-(3,4-dimethoxyphenyl)-2-isopropylvaleronitrile,
  (S)-5-[(3-methoxyphenethyl)-methylamino]-2-(3,4-dimethoxyphenyl)-2-isopropylvaleronitrile,
(RS)-5-[(3,5-dimethoxyphenethyl)-methylamino]-2-(3,5-dimethoxyphenyl)-2-isopropylvaleronitrile and its enantiomers.
(RS)-5-[(phenethyl)-methylamino]-2-(3,4,5-trimethoxyphenyl)-2-isopropylvaleronitrile and its enantiomers,
(RS)-5-[(3-trifluoromethylphenethyl)-methylamino]-2-(3,4,5-trimethoxyphenyl)-2-isopropylvaleronitrile and its enantiomers.

The superior action of the compounds can be demonstrated, for example, by the inhibition of the serotonin-induced increase in blood pressure in the pithed rat on intravenous administration.

In male Sprague-Dawley rats weighing 220–280 g and anesthetized with amobarbital (120 mg/kg of body weight, administered intraperitoneally), the carotid artery and the jugular vein are cannulized, the vaguas and sympathetic nerves are cut through on both sides, and the animals are connected to a respiratory pump. Pithing is effected by means of a rod through the orbit. Injections of 0.0215 mg/kg of serotonin administered intravenously increase the mean arterial pressure of 53±0.6 mmHg by 80 ±1.2 mmHg (n=95) in control animals which have not been pretreated. The criterium for effectiveness of a substance is the relative inhibition (Δ%) of the serotonin-induced increase in blood pressure (ΔmmHg). The valuation was effected quantitatively as an analysis of the linear regression (y=a+b x) of log dose (mg/kg) and relative inhibition (Δ%) of the serotonin-induced increase in blood pressure. For comparison, the dose which inhibits the serotonin-induced increase in blood pressure by 50% was calculated as the ED 50%. The following values were obtained:

| Substance of example | ED 50% |
| --- | --- |
| 1 | 0.0464 |
| 2 | 0.0730 |
| 3 | 0.0464 |
| 4 | 0.0318 |
| 5 | 0.0464 |
| 6 | 0.1 |
| 7 | 0.1 |
| 8 | 0.0499 |
| 13 | 0.0464 |
| 14 | 0.0464 |
| 17 | 0.1 |
| 19 | 0.1 |
| 20 | 0.1 |
| 24 | 0.1 |
| 27 | 0.0464 |
| 30 | 0.1 |
| 31 | 0.464 |
| 32 | 0.316 |
| 36 | 0.0464 |

-continued

| Substance of example | ED 50% |
| --- | --- |
| 37 | 0.0464 |
| 38 | 0.0681 |
| 39 | 0.0395 |
| 40 | 0.1 |
| 41 | 0.1 |
| 42 | >0.0464 (19%) |
| 43 | 0.215 |
| 44 | 0.0464 |
| 57 | 0.0423 |
| 58 | 0.0201 |
| 59 | 0.0464 |
| 60 | 0.0464 |
| 61 | 0.0681 |
| Verapamil | 0.363 |
| Gallopamil | 0.1 (22%) |

After intravenous administration, the novel compounds have a serotonin-antagonistic action on pithed rats which is up to 11 times more powerful than that of verapamil.

The compounds can be administered orally or parenterally in a conventional manner. The dose depends on the age, condition and weight of the patient and on the route of administration. As a rule, the daily dose of active compound is about 0.1–10 mg/kg of body weight in the case of oral administration and from 0.01 to 1.0 mg/kg of body weight in the case of parenteral administration. Usually, daily doses of from 1 to 5 mg/kg are used for oral administration and from 0.05 to 0.25 mg/kg for parenteral administration.

The novel active compounds can be converted to the conventional pharmaceutical administration forms, such as tablets, coated tablets, solutions, emulsions, powders, capsules or depot forms, and the conventional pharmaceutical auxiliaries and the usual manufacturing methods can be employed for their preparation. Appropriate tablets can be obtained, for example, by mixing the active compounds with known auxiliaries, for example inert diluents, such as calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate.

The tablets may furthermore consist of a plurality of layers. Coated tablets can be prepared by a corresponding method by coating cores, produced similarly to the tablets, with agents usually employed in tablet coatings, for example Kollidon or shellac, gum arabic, talc, titanium dioxide or sugar. In order to achieve a depot effect or to avoid incompatibility, the core too may consist of a plurality of layers. Furthermore, the tablet shell may also consist of a plurality of layers in order to achieve a depot effect, and the auxiliaries mentioned above in connection with the tablets may be used.

Syrups of the novel active compounds or combinations of active compounds may additionally contain a sweetener, such as saccharin, cyclamate, glyerol or sugar, and a flavor improver, e.g. flavorings such as vanillin or orange extract.

They may also contain suspending agents or thickeners, such as sodium carboxymethylcellulose, wetting agents, for example condensates of fatty alcohols with ethylene oxide, or preservatives, such as p-hydroxybenzoates.

Injectable solutions are prepared in a conventional manner, for example with the addition of preservatives, such as p-hydroxybenzoates, or stabilizers, such as Komplexons, and are introduced into injection bottles or ampoules.

Capsules containing the active compounds or combinations of active compounds can be prepared, for example, by mixing the active compounds with inert carriers, such as lactose or sorbitol, and encapsulating the mixture in gelatin capsules.

Suitable suppositories can be produced, for example, by mixing the active compounds or combinations of active compounds intended for this purpose with conventional carriers, such as neutral fats or polyethylene glycol or its derivatives.

The examples which follow illustrate the invention without restricting it.

EXAMPLE 1

5-[(3,5-Dimethoxyphenethyl)-methylamino]-2-(3-methoxyphenyl)-2-isopropylvaleronitrile A stirred solution of 18.9 g (0.1 mole) of α-isopropyl-3-methoxyphenylacetonitrile and 27.2 g (0.1 mole) of N-(3-chloropropyl)-N-methyl-3,5-dimethoxyphenethylamine in 100 ml of toluene was heated to 85° C. Thereafter, 8 g (about 0.1 mole) of a 50% strength suspension of sodium amide in toluene were added dropwise in the course of 2 hours. The reaction solution was stirred for a further 15 minutes at 85° C. and left to cool, after which 200 ml of ice water were added. The toluene phase was separated off and washed twice with water, after which the toluene was distilled off under reduced pressure. The oily residue was dissolved in 150 ml of ethanol and 10 g of oxalic acid were added. The precipitated hydrogen oxalate was filtered off under suction and recrystallized from 200 ml of ethanol. 43.4 g (85%) of hydrogen oxalate of melting point 159°–161° C. were isolated.

EXAMPLE 2

5-[(3-Methoxyphenethyl)-methylamino]-2-(3,5-dimethoxyphenyl)-2-isopropylvaleronitrile 38.3 g (0.1 mole) of 5-[(3-methoxyphenethyl)-methylamino]-2-(3,5-dimethoxyphenyl)-valeronitrile were dissolved in 200 ml of toluene, and the stirred solution was refluxed with 4.7 g (0.12 mole) of powdered sodium amide for 1 hour. Thereafter, a solution of 15.7 g (0.12 mole) of isopropylbromide in 30 ml of toluene was added dropwise in the course of 60 minutes, and refluxing was continued for a further 2 hours. The cooled reaction mixture was poured into water, the toluene phase was washed several times with water and the toluene was then distilled off. The residue was dissolved in 100 ml of isopropanol, and ethanolic hydrochloric acid was added. The hydrochloride was recrystallized from isopropanol. 46.9 g (92%) of a hydrochloride of melting point 141°–143° C. were isolated.

EXAMPLE 3

5-[(Phenethyl)-methylamino]-2-(3-methoxyphenyl)-2-isopropylvaleronitrile 13.5 g (0.1 mole) of 3-methoxyphenylacetonitrile were dissolved in 15 ml of toluene, and 52 g (0.8 mole) of 85% strength potassium hydroxide powder and 0.2 g of tris(3,6-dioxaheptyl)-amine were added. Thereafter, 12.3 g (0.1 mole) of isopropyl bromide were added dropwise to the stirred mixture at a rate such that the reaction temperature did not exceed 50° C. When the addition was complete, stirring was continued for 2 hours at 50° C., after which a solution of 21.2 g (0.1 mole) of N-(3-chloropropyl)-N-methylphenethylamine in 20 ml of toluene was added at 90° C. The reaction mixture was stirred for a further 3 hours at 90° C. and cooled, after which 100 ml of water were added and the toluene phase was separated off. The toluene was distilled off to give a yellow oil, which was chromatographed over a silica gel column using a solvent mixture consisting of 9:1:0.5 methylene chloride/acetone/methanol. The chromatographically pure base was dissolved in ethyl acetate, and the hydrochloride was precipitated with ethanolic hydrochloric acid. 26.1 g (65%) of a product of melting point 154°–156° C. were obtained.

EXAMPLE 4

5-[(3-Methoxyphenethyl)-methylamino]-2-(3-methoxyphenyl)-2-isopropylvaleronitrile 47.1 g (0.1 mole) of [(3-methoxyphenethyl)amino]2-(3-methoxyphenyl)-2-isopropylvaleronitrile were dissolved in 50 ml of formic acid at room temperature and 11.9 ml of 35% strength aqueous formalin solution (0.15 mole) were added, after which the mixture was heated on a waterbath until evolution of carbon dioxide was complete. After cooling the reaction solution was diluted with water and rendered alkaline by adding ammonia, and the precipitated base was extracted with ether. The ethereal solution was washed several times with water and dried with potassium carbonate, after which the ether was distilled off. The residue was dissolved in ethyl acetate, and ethanolic hydrochloric acid was added. 37.9 g (88%) of the hydrochloride of melting point 102°–104° C. were precipitated.

EXAMPLE 5

5-[(Phenethyl)methylamino]-2-(3,5-dimethoxyphenyl)-2-isopropylvaleronitrile 29.5 g (0.1 mole) of α-isopropyl-α-(3-chloropropyl)-3,5-dimethoxyphenylacetonitrile and 13.5 g (0.1 mole) of N-methylphenethylamine were dissolved in 45 ml of hexamethylphosphorotriamide, and 30 g of powdered anhydrous potassium carbonate were added. The reaction mixture was heated at 80° C. for 4 hours and then cooled, after which 500 ml of water were added and the mixture was extracted twice with ether. The ether phase was washed several times with water and dried over potassium carbonate, and the ether was distilled off. The resulting base was converted to the hydrochloride. 34.8 g (81%) of a product of melting point 126°–127° C. were obtained.

EXAMPLE 6

5-[(4-Chlorophenethyl)-methylamino]-2-(3,5-dimethoxyphenyl)-2-isopropylvaleronitrile 29.0 g (0.1 mole) of 5-methylamino-2-(3,5-dimethoxyphenyl)-2-isopropylvaleronitrile and 21.0 g (0.12 mole) of 4-chlorophenethyl chloride were reacted similarly to Example 5, and 27.9 g (60%) of base were isolated after chromatographic purification. The base was converted to the amidosulfonate. Mp. 122°–123° C.

EXAMPLE 7

5-[(3,4-Dichlorophenethyl)-methylamino]-2-(3,5-dimethoxyphenyl)-2-isopropylvaleronitrile 27.5 g (0.1 mole) of 4-(3,5-dimethoxyphenyl)-4-cyano-5-methylhexanal and 20.4 g (0.1 mole) of N-methyl3,4-dichlorophenethylamine were dissolved in 100 ml of toluene. 4.6 g (0.1 mole) of formic acid were added to the solution at room temperature. The reaction mixture was refluxed until evolution of gas died down.

Aqueous potassium carbonate solution was added to the cooled reaction solution, the liberated amine was extracted with ether, the ethereal phase was washed several times with water and dried and the ether was distilled off.

The resulting oily base was dissolved in isopropanol, and ethanolic hydrochloric acid was added. Recrystallization from isopropanol gave 46 g (92%) of 5-[(3,4-dichlorophenethyl)-methylamino]-2-(3,5-dimethoxyphenyl)-2-isopropylvaleronitrile hydrochloride of melting point 147°–148.5° C.

EXAMPLE 8

5-[(3-Trifluoromethylphenethyl)-methylamino]-2-(3,5-dimethoxyphenyl)-2-isopropylvaleronitrile A mixture of 29.0 g (0.1 mole) of 2-(3,5-dimethoxyphenyl)-2-isopropyl-5-methylaminovaleronitrile (prepared by reacting α-isopropyl-3,5-dimethoxyphenylacetonitrile and 3-methylformamido-1-chloropropane in the presence of sodium hydride and then eliminating the formyl group by means of hydrochloric acid) and 18.8 g (0.1 mole) of 3-trifluoromethylphenylacetaldehyde was reduced catalytically with 400 mg of 5% strength palladium on carbon in 100 ml of toluene under atmospheric pressure at from 25 to 30° C. for 20 hours. After the catalyst had been removed, the toluene solution was washed several times with water and dried with potassium carbonate, after which the toluene was distilled off. The residue was dissolved in isopropanol, and ethanolic hydrochloric acid was added. Crystallization from isopropanol gave 39.9 g (80%) of 5-[(3-trifluoromethylphenethyl)-methylamino]-2-(3,5-dimethoxyphenyl)-2-isopropylvaleronitrile of melting point 136°–138° C.

EXAMPLE 9

5[(3,5-Dimethoxyphenethyl)-methylamino]-2-(3,5-dimethoxyphenyl-2-(n-propyl)-valeronitrile In a hydrogenation apparatus, 40.8 g (0.15 mole) of 4-(3,5-dimethoxyphenyl)-4-cyanoheptanoic acid nitrile were dissolved in 170 ml of isopropanol, 7 g of 5% strength Pd/C were added and the apparatus was flushed with nitrogen. After the addition of 2 ml of aqueous cetyltrimethylammonium hydroxide solution, a stream of hydrogen was passed through the apparatus with vigorous stirring, and the stock vessel was filled with hydrogen. Thereafter, 29.3 g (0.15 mole) of N-methyl-3,5-dimethoxyphenethylamine were added to the reaction mixture, and hydrogenation was carried out at from 50° to 60° C. under slightly excess hydrogen pressure. After 2 hours, the hydrogenation was complete.

The catalyst was separated off, after which the isopropanol solution was evaporated down under reduced pressure, the residue was taken up in ether and the solution was shaken several times with sodium chloride solution. The base was then removed from the ethereal phase with aqueous amidosulfonic acid solution. The acidic solution was extracted several times by shaking with ether, after which the base was liberated with aqueous potassium carbonate solution and purified by column chromatography.

Analysis: calculated: C 71.3; H,8.4; N,6.2. found: C, 71.5; H, 8.5; N, 6.1.

EXAMPLE 10

5-[(3,5-Dimethoxyphenethyl)-methylamino]-2-(3,5-dimethoxyphenyl)-2-phenylvaleronitrile 32.4 g (0.1 mole) of 5-methylamino-2-(3,5-dimethoxyphenyl)-2-phenylvaleronitrile and 17.7 g (0.1 mole) of 3,5-dimethoxyphenylacetonitrile were converted in a manner similar to that described in Example 9 to give 41.6 g (85%) of base, which was purified by column chromatography.

Analysis: calculated: C, 73.7; H, 7.4; N 5.7. found: C, 73.6; H, 7.5; N 5.7.

The following were obtained in a similar manner:

(11) 5-[(3,5-dimethoxyphenethyl)-methylamino]-2-(3,5-dimethoxyphenyl)-2-(cyclohexen-1-yl)-valeronitrile
Analysis: calculated: C, 73.1; H, 8.2.; N 5.7. found: C, 73.2.; H, 8.3; N, 5.6.

(12) 5-[(3,5-dimethoxyphenethyl)-methylamino]-2-(3,5-dimethoxyphenyl)-2-benzylvaleronitrile
Analysis: calculated: C, 74.1; H 7.6; N 5.6 found: C, 73.9; H, 7.7., N 5.4.

(13) 5-[(3-methoxyphenethyl)-methylamino]-2-phenyl-2-isopropylvaleronitrile
Analysis: calculated: 79 1., H, 8.9.; N, 7.7. found: C, 79.0, H, 9.0; N 7.7.

(14) 5-[(3,5-dimethoxyphenethyl)-methylamino]-2-phenyl-2-isopropylvaleronitrile-aminosulfonate, melting point 119° to 120° C.

(15) 5-[(3-chlorophenethyl)-methylamino]-2-(3,5-dimethoxyphenyl)-2-isopropylvaleronitrile
Analysis: calculated: C, 70.0; H, 7.8; N, 6.5; Cl, 8.3 found: C, 70.1; H, 7.7; N, 6.5; Cl 8.2.

(16) 5-[(3,5-dichlorophenethyl)-methylamino]-2-(3,5-dimethoxyphenyl)-2-isopropylvaleronitrile
Analysis: calculated: C, 64.8.: H, 7.0; N, 6.0; Cl 15.3. found: 64.9; H, 6.9; N, 6.0; Cl, 15.4.

(17) 5-[(3,5-dimethoxyphenethyl)-methylamino]-2-(3-ethoxy-phenyl)-2-isopropylvaleronitrile hydrochloride, mp. 124°–126° C.

(18) 5-[(3-ethoxyphenethyl)-methylamino]-2-(3,5-dimethoxyphenyl)-2-isopropylvaleronitrile hydrochloride, mp. 113°–115° C.

(19) 5-[(3,5-diethoxyphenethyl)-methylamino]-2-(3,5-dimethoxyphenyl)-2-isopropylvaleronitrile hydrochloride, mp. 117°–119° C.

(20) 5-[(3,4-xylylethyl)-methylamino]-2-(3,5-dimethoxyphenyl)-2-isopropylvaleronitrile hydrochloride, mp. 136.5°–138.5° C.

(21) 5-[(3,5-xylylethyl)-methylamino]-2-(3,5-dimethoxyphenyl)-2-isopropylvaleronitrile
Analysis: calculated: C, 76.7; H, 9.1N, 6.6. found: C, 76.5; H, 9.0; N, 6.5.

(22) 5-[(3,5-dimethoxyphenethyl)-methylamino]-2-(3,5-xylyl)-2-isopropylvaleronitrile
Analysis: calculated: C, 76.7 H, 9.1, N, 6.6. found: C, 76.9; H, 9.2; N, 6.6.

(23) 5-[(3-nitrophenethyl)-methylamino]-2-(3,5-dimethoxyphenyl)-2-isopropylvaleronitrile
Analysis: calculated C, 68.3; H, 7.6; N, 9.6. found: C, 68.2; H, 7.6; N, 9.5.

(24) 5-[(3,5-diethoxyphenethyl)-methylamino]-2-phenyl-2-isopropylvaleronitrile
Analysis: calculated: C, 76.7; H, 9.1, N)6.6. found: C, 76.8; H,9.0; N, 6.5.

(25) 5-[(3-methoxyphenethyl)-methylamino]-2,2-diphenylvaleronitrile
Analysis: calculated C, 81.4; H, 7 6; N, 7.0. found: C, 81.2; H, 7.7; N, 6.9.

(26) 5-[(3,5-dimethoxyphenethyl)-methylamino]-2,2-diphenylvaleronitrile
Analysis: calculated: C, 78.5; H, 7.5; N, 6.5. found: C, 78.6; H, 7.3; N, 6.5.

(b 27) 5-[(3,4-methylenedioxyphenethyl)-methylamino]-2-(3,5-dimethoxyphenyl)-2-isopropylvaleronitrile
Analysis: calculated: C, 71.2; H, 7.8; N/6.4. found; C, 71.0; H, 8.0; N, 6.4.

(28) 5-[(3,4-ethylenedioxyphenethyl)-methylamino]-2-(3,5-dimethoxyphenyl)-2-isopropylvaleronitrile
Analysis: calculated: C, 71.7; H, 8.0; N, 6.2. found: C, 71.5; H, 7.9; N, 6.1.

(29) 5-[(1,3-benzodioxanyl-6-ethyl)-methylamino]-2-(3,5-dimethoxyphenyl)-2-isopropylvaleronitrile
Analysis: calculated: C, 71.7; H, 8.0; N 6.2. found: C, 71.9; H, 8.1; N,6.2.

(30) 5-[(3,5-dimethoxyphenethyl)-methylamino]-2-($\beta,\beta,\beta$-trifluoroethoxyphenyl)-2-isopropylvaleronitrile hydrogen oxalate, mp. 138°–139° C.

(31) 5-[(phenethyl)-methylamino]-2-(3-chlorophenyl)-2-allylvaleronitrile hydrochloride, mp. 132°–136° C.

(32) 5-[(3-methoxyphenethyl)-methylamino]-2-(3-chlorophenyl)-2-allylvaleronitrile
Analysis: calculated: C, 72.6; H, 7.4.; Cl, 8.9; N, 7.1. found: C, 72.1; H, 7.4.; Cl, 9.0; N, 7.2.

(33) 5-[(3-trifluoromethoxyphenethyl)-methylamino]-2-(3-trifluoromethoxyphenyl)-2-isopropylvaleronitrile hydrogen oxalate, mp. 155°–157° C.

(34) 5-[(3,5-dimethoxyphenethyl)-methylamino]-2-(3-trifluoromethoxyphenyl)-2-isopropylvaleronitrile hydrogen oxalate, mp. 152°–157° C.

(35) 5-[(3,4-dichlorophenethyl)-methylamino]-2-(3-ethoxy-phenyl)-2-isopropylvaleronitrile hydrochloride, mp. 165°–168° C.

(36) 5-[(3-methoxyphenethyl)-methylamino]-2-(3,4,5-trimethoxyphenyl)-2-isopropylvaleronitrile hydrochloride, mp. 162°–163° C.

(37) 5-[(3-nitrophenethyl)-methylamino]-2-(3,4,5-trimethoxyphenyl)-2-isopropylvaleronitrile hydrochloride, mp. 157°–158° C.

(38) 5-[(3-chlorophenethyl)-methylamino]-2-(3,4,5-trimethoxyphenyl)-2-isopropylvaleronitrile hydrochloride, mp. 183°–185° C.

(39) 5-[(1,3-benzodioxan-6-ylethyl)-methylamino]-2-(3,4,5-trimethoxyphenyl)-2-isopropylvaleronitrile hydrochloride, mp. 198°–201° C.

(40) 5-[(3,4-dichlorophenethyl)-methylamino]-2-(3,4-dimethoxyphenyl)-2-isopropylvaleronitrile amidosulfonate, mp. 90° C.

(41) 5-[(3,5-dimethoxyphenethyl)-methylamino]-2-(3,4-dichlorophenyl)-2-isopropylvaleronitrile hydrochloride, mp. 96°–100° C.

(42) 5-[(3,5-dimethoxyphenethyl)-methylamino]-2-(4-chlorophenyl)-2-isopropylvaleronitrile hydrochloride, mp. 143°–147° C.

(43) 5-[(3,5-dimethoxyphenethyl)-methylamino]-2-(1,2,3,4-tetrahydronaphth-2-yl)-2-isopropylvaleronitrile hydrogen oxalate, mp. 170°–175° C.

(44) 5-[(3,4-dimethoxyphenethyl)-methylamino]-2-(3-ethoxy-phenyl)-2-isopropylvaleronitrile
Analysis: calculated: C, 73.9; H)8 7; N)6.4. found: C, 73.7; H, 8.8; N, 6.5.

(45) 5-[(3,4,5-trimethoxyphenethyl)-methylamino]-2-(3,5-dimethoxyphenyl)-2-isopropylvaleronitrile hydrochloride, mp. 122°–123° C.

(46) 5-[(3-methoxyphenethyl)-ethylamino]-2-(3,4,5-trimethoxyphenyl)-2-isopropylvaleronitrile hydrochloride, mp. 148°–149° C.

(47) 5-[(3-ethoxyphenethyl)-methylamino]-2-(3-ethoxyphenyl)-2-isopropylvaleronitrile hydrochloride, mp. 138°–140° C.

(48) 5-[(1,3-benzodioxan-6-ylethyl)-methylamino]-2-(3,5-diethoxyphenyl)-2-isopropylvaleronitrile hydrochloride, mp. 146°–147° C.

(49) 5-[(3-ethoxyphenethyl)-methylamino]-2-(3,5-dimethoxyphenyl)-2-isopropylvaleronitrile hydrochloride, mp. 113°–115° C.

(50) 5-[(3,4,5-triethoxyphenethyl)-methylamino]-2-(3,5-dimethoxyphenyl)-2-isopropylvaleronitrile hydrochloride, mp. 144°–145° C.

(51) 5-[(4-fluorophenethyl)-methylamino]-2-(3,5-dimethoxyphenyl)-2-isopropylvaleronitrile hydrogen oxalate, mp. 146°–148° C.

(52) 5-[(3-fluoro-4-methoxyphenethyl)-methylamino]-2-(3,5-dimethoxyphenyl)-2-(3,5-dimethoxyphenyl)-2-isopropylvaleronitrile hydrochloride, mp. 114°–117° C.

(53) 5-[(4-methoxyphenethyl)-methylamino]-2-(3,5-dimethoxyphenyl)-2-isopropylvaleronitrile hydrochloride, mp. 128°–130° C.

(54) 5-[(3,4-dimethoxyphenethyl)-methylamino]-2-(3,5-dimethoxyphenyl)-2-isopropylvaleronitrile hydrochloride, mp. 162° C.

(55) 5-[(phenethyl)-methylamino]-2-(3-chlorophenyl)-2-isopropylvaleronitrile
Analysis: calculated: C;74.9 H, 7.9; N, 7.6. found: C, 74.8; H, 7.7; N, 7 5.

(56) 5-[(4-fluorophenethyl)-methylamino]-2-phenyl-2-isopropylvaleronitrile
Analysis: calculated: C;78.4; H, 8.3; N, 8.0 found: C, 78.3; H, 8.2; N, 7.9.

The following known compounds were obtained in a similar manner:

(57) (RS)-5-[(3-methoxyphenethyl)-methylamino]-2-(3,4-dimethoxyphenyl)-2-isopropylvaleronitrile hydrochloride, mp. 123°–125° C.

(58) (S)-5-[(3-methoxyphenethyl)-methylamino]-2-(3,4-dimethoxyphenyl)- 2-isopropylvaleronitrile hydrochloride, mp. 116°–118° C.

(59) 5-[(3,5-dimethoxyphenethyl)-methylamino]-2-(3,5-dimethoxyphenyl)-2-isopropylvaleronitrile hydrochloride, mp. 145°–147° C.

(60) 5-[(phenethyl)-methylamino]-2-(3,4,5-trimethoxyphenyl)-2-isopropylvaleronitrile hydrochloride, mp. 156°–158° C.

(61) 5-[(3-trifluoromethylphenethyl)-methylamino]-2-(3,4,5-trimethoxyphenyl)-2-isopropylvaleronitrile hydrochloride, mp. 163°–165° C.

EXAMPLE 62

Tablets having the following composition were pressed in a conventional manner on a tablet press:
40 mg of the substance of Example 3
120 mg of corn starch
13.5 mg of gelatin
45 mg of lactose
2.25 mg of Aerosil ® (chemically pure, submicroscopically finely divided silica)
6.75 mg of potato starch (as a 6% strength paste).

EXAMPLE 63

Coated tablets having the following composition were prepared in a conventional manner:
20 mg of the substance of Example 3
60 mg of core material
60 mg of sugar-coating material
The core material consisted of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consisted of parts of sucrose, 2 parts of corn starch, 2 parts of calcium carbonate and 1 part of talc. The coated tablets prepared in this manner were then provided with a coating resistant to gastric juice.

EXAMPLE 64

10 g of the substance of Example 3 were dissolved in 5000 ml of water with the addition of NaCl and the pH was brought to 6.0 with 0.1N NaOH so that a blood-isotonic solution was formed. 5 ml of this solution in each case were introduced into ampoules and sterilized.

We claim:

1. A phenylacetonitrile which is substituted by basic groups and is the formula I

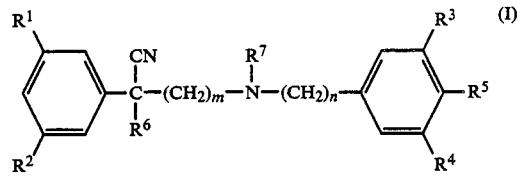

where
$R^1$ and $R^2$ are identical or different and are each hydrogen, halogen, $C_1$–$C_3$-alkyl, nitro, methoxy or ethoxy, $R^3$ and $R^4$ are identical or different and are each hydrogen, halogen, trifluoromethyl, $C_1$–$C_3$-alkyl, nitro, methoxy or ethoxy,
$R^5$ is hydrogen, halogen or $C_1$–$C_3$-alkyl,
or $R^3$ and $R^5$ together may furthermore form a methylenedioxy, ethylenedioxy or 1,3-dioxatetramethylene group, and one or more of the radicals $R^1$ to $R^5$ must not be hydrogen and, if $R^6$ is isopropyl, $R^7$ is methyl, m is 3 and n is 2, all of $R^1$, $R^2$ $R^3$ and $R^4$ cannot simultaneously by methoxy or ethoxy, $R^6$ is a saturated hydrocarbon radical of not more than 6 carbon atoms, $C_3$–$C_8$-cycloalkyl or $C_5$–$C_8$-cycloalkenyl, or is phenyl. having substituents the same as those defined by $R^3$, $R^4$ or $R^5$, above
$R^7$ is $C_1$–$C_4$-alkyl,
m is from 2 to 4 and
n is 2 or 3
or its antipodes or salts with physiologically tolerated acids.

2. A compound selected from the group consisting of
(RS)-5-((3-nitrophenethyl)-methylamino)-2-(3,4,5-trimethoxyphenyl)-2-isopropylvaleronitrile,
(RS)-5-((3-chlorophenethyl)-methylamino)-2-(3,4,5-trimethoxyphenyl)-2-isopropylvaleronitrile,
(RS)-5-((3,4-dichlorophenethyl)-methylamino)-2-(3,4-dimethoxyphenyl)-2-isopropylvaleronitrile,
(RS)-5-((3,5-dimethoxyphenethyl)-methylamino)-2-(3,4-dichlorophenyl2-isopropylvaleronitrile,
(RS)-5-((3,5-dimethoxyphenethyl)-methylamino)-2-(4-chlorophenyl)-2-isopropylvaleronitrile, (RS)-5-((3,5-dimethoxyphenethyl)-methylamino)-2-(1,2,3,4-tetrahydronaphth-2-yl)-2-isopropylvaleronitrile, (RS)-5-((3,4-dimethoxyphenethyl)-methylamino)-2-(3-ethoxyphenyl)-2-isopropylvaleronitrile, (RS)-5-(3,4,5-trimethoxyphenethyl)-methylamino)-2-(3,5-dimethoxyphenyl)-2-isopropylvaleronitrile, (RS)-5-((4-fluorophenethyl)-methylamino)-2-phenyl-2-isopropyl-valeronitrile, or their antipodes or salts with physiologically tolerated acids.

3. A therapeutic composition for treating cerebrovascular disorders, hypertension, coronary heart desease, platelet aggregation or peripheral vascular disorders, said composition having a serotonin-antagonistic activity and a calcium-antagonistic activity, which composition comprise a pharmaceutically acceptable carrier and an effective amount of a compound according to claim 1 as the active compound.

4. The method of treating cerebrovascular disorders, hypertension, coronary heart disease, platelet aggregation or peripheral vascular disorders in a patient suffering therefrom, which comprises administering an effective amount of a compound of the formula XIV

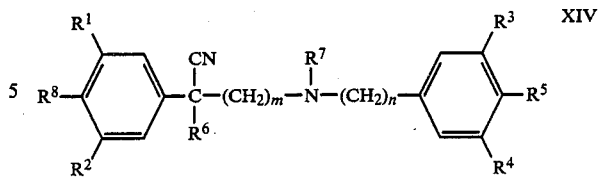

where $R^1$, $R^2$, $R^3$, $R^4$, $R^5$ and $R^8$ are identical or different and are each hydrogen, halogen, trifluoromethyl, $C_1-C_3$-alkyl, nitro, methoxy or ethoxy and $R^3$ and $R^5$ together may furthermore form a methylenedioxy, ethylenedioxy or 1,3-dioxatetramethylene group and one or more of the radicals $R^1$ to $R^5$ must not be hydrogen and, if $R^6$ is isopropyl, $R^7$ is methyl, m is 3, and n is 2, all of $R^1$, $R^2$, $R^3$ and $R^4$ cannot simultaneously be methoxy or ethoxy, $R^6$ is a saturated hydrocarbon radical of not more than 6 carbon atoms, $C_3-C_8$-cycloalkyl or $C_5-C_8$-cycloalkenyl or is phenyl having substituents the same as those defined by $R^1$, $R^2$ or $R^3$, above $R^7$ is $C_1-C_4$ and n is 2 or 3 or its antipodes or salts with physiologically tolerated acids.

5. A therapeutic composition for treating cerebrovascular disorders, hypertension, coronary heart disease, platelet aggregation or peripheral vascular disorders, said composition having a serotonin-antagonistic activity and a calcium-antagonistic activity, which composition comprises a pharmaceutically acceptable carrier and an effective amount of a compound according to claim 1 or 2 as the active compound.

* * * * *

UNITED STATES PATENT AND TRADEMARK OFFICE
CERTIFICATE OF CORRECTION

PATENT NO. : 4,968,717

DATED : November 6, 1990

INVENTOR(S) : Liliane UNGER et al.

It is certified that error appears in the above-identified patent and that said Letters Patent is hereby corrected as shown below:

Claim 1, line 16 (Column 16, line 48)

after "simultaneously" delete "by" and insert --be--

Claim 1, line 19 (Column 16, line 51)

after "phenyl" delete ","

Claim 2, line 9 (Column 16, line 66)

"(3,4-dichlorophenyl2-" should read --(3,4-dichlorophenyl-2---

Claim 3, line 6 (Column 17, line 26)

"comprise" should read --comprises--

Signed and Sealed this

Fifth Day of May, 1992

Attest:

DOUGLAS B. COMER

Attesting Officer

Acting Commissioner of Patents and Trademarks